(12) United States Patent
Pfeifer

(10) Patent No.: US 8,999,272 B2
(45) Date of Patent: Apr. 7, 2015

(54) HOLDER FOR A CAPTURE DEVICE

(75) Inventor: Gerhard Pfeifer, Wetzlar (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 1040 days.

(21) Appl. No.: 12/872,753

(22) Filed: Aug. 31, 2010

(65) Prior Publication Data

US 2011/0048142 A1    Mar. 3, 2011

(30) Foreign Application Priority Data

Sep. 1, 2009   (DE) .......................... 10 2009 029 078

(51) Int. Cl.
   *G01N 15/06*    (2006.01)
   *G02B 21/34*    (2006.01)
   *G01N 1/28*    (2006.01)

(52) U.S. Cl.
   CPC .......... *G02B 21/34* (2013.01); *G01N 2001/284* (2013.01)

(58) Field of Classification Search
   CPC ............................... G01N 1/06; B01L 3/5082
   USPC ............................................ 422/65, 561, 560
   See application file for complete search history.

(56) References Cited

U.S. PATENT DOCUMENTS

| | | |
|---|---|---|
| 2,587,094 A | 2/1952 | Budnick et al. |
| 3,865,340 A | 2/1975 | Ellis |
| 4,116,548 A | 9/1978 | Persson |
| 4,180,252 A | 12/1979 | Cushenbery |
| 4,425,023 A | 1/1984 | Matsumoto et al. |
| 5,339,749 A | 8/1994 | Hirose |
| 5,895,628 A * | 4/1999 | Heid et al. ........................ 422/65 |
| 6,742,768 B2 * | 6/2004 | Alba ............................. 254/122 |
| 7,044,008 B1 | 5/2006 | Schutze et al. |
| 2002/0061261 A1 | 5/2002 | Pfeifer et al. |
| 2006/0012773 A1 | 1/2006 | Schutze et al. |
| 2007/0031816 A1* | 2/2007 | Schuetze et al. ................... 435/4 |

FOREIGN PATENT DOCUMENTS

| | | |
|---|---|---|
| DE | 2 349 680 A | 4/1974 |
| DE | 28 03 020 A1 | 9/1978 |
| DE | 31 02 972 C2 | 11/1981 |
| DE | 100 57 292 C2 | 7/2002 |
| DE | 102 28 818 B4 | 1/2004 |
| DE | 102 54 229 A1 | 6/2004 |
| DE | WO 2008/034833 A2 | 3/2008 |
| EP | 1 890 126 A1 | 2/2008 |
| WO | WO 01/73397 A1 | 10/2001 |

* cited by examiner

*Primary Examiner* — Sally Merkling
(74) *Attorney, Agent, or Firm* — Foley & Lardner LLP

(57) ABSTRACT

The present invention relates to a holder for at least one capture device (30) for collecting microdissected specimens, having a holding element (2) in which the at least one capture device (30) is to be arranged, the holding element (2) being transferable into a working position in order to collect microdissected specimens, the holding element (2) being mounted by way of at least two levers (3a, 3b) in a frame (1) of the holder (40), and being vertically displaceable relative to said frame (1) by way of a displacement of the levers (3a, 3b).

14 Claims, 10 Drawing Sheets

HOLDER FOR A CAPTURE DEVICE

CROSS-REFERENCE TO RELATED PATENT APPLICATIONS

The right of foreign priority is claimed under 35 U.S.C. §119(a) based on Federal Republic of Germany Application No. 10 2009 029 078.8, filed Sep. 1, 2009, the entire contents of which, including the specification, drawings, claims and abstract, are incorporated herein by reference.

BACKGROUND OF THE INVENTION

The present invention relates to a holder for at least one capture device for collecting microdissected specimens cut out from a microscopic sample.

DE 100 57 292 C2 discloses an apparatus for receiving microdissected specimens, having at least one receptacle for collecting microdissected specimens, said apparatus being shiftable relative to an X/Y stage. In order to produce microdissected specimens, a laser beam is guided through the main objective of a microscope with which a prepared specimen is being examined or imaged. The prepared specimen is located as a rule on a suitable film, so that with the aid of the laser beam focused onto the film, a specimen region of interest can be cut out of the prepared specimen. The specimen region cut out in this fashion, i.e. the microdissected specimen that has been produced, falls into a container arranged below the prepared specimen. To allow reliable collection of the cut-out prepared specimen (typical diameters are between 10 and 50 µm) to be ensured, the container, specifically its opening, must be brought close enough to the prepared specimen. This action also ensures that undesired foreign particles present in the air do not get into the container.

The aforesaid DE 100 57 292 C2 provides for this purpose, between the prepared specimen and container, a contamination prevention plate which comprises a cutout that leaves open only the relevant container for the collection of microdissected specimens, while the other containers are covered. Each container is arranged in this case in a separate holding element; by pivoting of a holding element about an axis extending parallel to the X/Y stage, said element is pivotable from a position inclined with respect to the X/Y stage into a working position in which the upper rim of the container aligns with the plane defined by the contamination prevention plate.

WO 2008/034833 A2 relates to a microscope system having a microdissection device; the object to be achieved here is to separate living cells from a culture or an agglomerate, by microdissection and without contamination risks. For this purpose, microdissection is to occur in a sterile environment. A description is given of various types of devices for receiving biological material with which microdissection can be carried out in a sterile environment. One such device for receiving biological material involves, for example, a frame- or lattice-shaped sample carrier having stretched over it a film on whose side oriented toward the carrier are located the samples to be cut out. The interior space in which the samples are located can be kept sterile by means of a cover. Located on the other side, facing away from the carrier, is a capture device that is arranged congruently below the sample carrier. Located in the capture elements of the capture device is a nutrient medium for cultivating the living cells that represent the samples to be cut out. Once the sample (individual cells or a cell group) has been cut out by means of a focused laser beam, it falls under the influence of gravitational force into the capture element located therebelow. The sterile atmosphere can be maintained in this context if the capture device is joined fixedly, and in externally sealed fashion, to the sample carrier.

A variety of sample carriers and corresponding capture devices for microdissection are known. For example, multiple containers arranged in matrix fashion (e.g. so-called multiwell plates or multidishes), Petri dishes, or frames made of glass or metal with film stretched on them, are used as sample carriers. The multiple containers or Petri dishes have a bottom made of laser-cuttable film. The frames with film stretched on them often have a standard specimen slide size. Also known are specimen slides with film adhesively bonded to them, which are used for microdissection purposes in inverted fashion, i.e. with the film and sample facing downward. Multiple capture elements arranged in matrix fashion, or other differently shaped containers, for example so-called PCT tubes, can be used as capture devices. In the case of PCR tubes, the cover that closes off the tube is often used as a collection element. It is also possible to utilize coated slides in which, for example, the capture regions are provided with a nutrient medium while the other regions have an antibacterial coating.

SUMMARY OF THE INVENTION

A problem with the known apparatuses for collecting microdissected specimens is that the collection container or capture device must be brought close enough to the prepared specimen, in particular when different capture devices and/or sample carriers are used for microdissection. The holding element, known from DE 100 57 292 C2, for a container only allows the container to be pivoted from a "rest" position to a "working" position; in the working position, the upper rim of the container must align with the contamination prevention plate. If it should happen that, when using a different capture device, the contamination prevention plate is farther away from the upper rim of the container, then with the known approach there exists no possibility for reducing the distance.

In the aforementioned application instance of microdissection, in the case of corresponding systems (Leica LMD 6500 and Leica LMD 7000) of the Applicant the laser beam is guided through the main objective of the microscope. As the prepared specimen is cut out, the main objective and sample remain at rest while the laser beam is suitably deflected in order to cut out the prepared specimen along a cut line. With other known laser microdissection units, the cutting laser beam is stationary and the microscope stage is displaced relative to it.

One object underlying the invention is that of describing a holder for at least one capture device for collecting a microdissected specimen, which holder can ensure that the capture device can be brought close enough to the prepared-specimen carrier in every application instance. At the same time, operation of the holder is to be simple and user-friendly.

A further object on which the present invention is based is that of describing a microdissection device in which a capture device for collecting a microdissected specimen can be brought, in every application instance, close enough to the prepared-specimen carrier from which the microdissected specimen derives. Lastly, the present invention is based on the object of describing a microscope system having such a microdissection device.

These objects are achieved respectively by a holder, and a microdissection device, and a microscope system having the features described herein.

The holder according to the present invention for at least one capture device for collecting microdissected specimens cut out of a microscopic sample, having a holding element in which the at least one capture device is to be arranged, the holding element being transferable into a working position in order to collect at least one microdissected specimen, is characterized in that the holding element is mounted by way of at least two levers in a frame of the holder, and is vertically displaceable relative to said frame by way of a displacement of the levers. Mounting of the holding element by way of at least two levers makes it possible for the holding element to be moved upward or downward in a spatially fixed position, suitably in a horizontal position or in a position parallel to an X/Y stage of a microdissection device. The capture device arranged in the holding element can thus be moved upward and downward in a consistent spatial, in particular horizontal, position. Different distances between a prepared-specimen carrier for microdissection and a capture device can thus be compensated for by use of the holder according to the present invention, by the fact that it is always possible to ensure, by corresponding vertical displacement of the holding element, that a capture element of the capture device can be brought close enough to the prepared specimen that is to be cut out.

It is advantageous in this context if, upon displacement of the levers, they execute a pivoting motion so as thereby to displace the holding element in terms of its height relative to the frame of the holder. Alternatively, it is also conceivable for the levers to perform, in the context of their displacement, a linear shift by means of which the holding element is then vertically displaced relative to the frame.

It is advantageous if each lever is (fixedly) coupled to a respective shaft that is in turn rotatably mounted in the frame of the holder. By rotation of a shaft, the associated lever is then also moved, i.e. it executes, for example, a pivoting motion that in turn results in an upward or downward motion of the holding element. The rotation of a shaft can also be converted, for example by means of a worm drive, into a translational motion from which the aforesaid linear shift of the associated lever then results.

Unless otherwise indicated in what follows, the explanations below are limited to a displacement of the levers by means of a pivoting motion of said levers. This is intended to facilitate comprehension of the construction and function of the holder according to the present invention, without limiting the scope of protection.

In order to synchronize the pivoting motions of the levers, it is advantageous if the levers are coupled in their pivoting motion by way of one or more coupling elements. For this purpose, for example, at least one coupling rod is present between two levers, the coupling rod usefully being rotatably joined by way of individual shafts to the levers. The shafts to which the levers are coupled can also be coupled in their rotation by way of coupling elements. The rotation of one shaft would then be transferred, by means of such a coupling element, to another shaft that co-rotates synchronously.

It has proven successful in practice if, for vertical displacement of the holding element, at least one shaft comprises a tool receptacle in order to pivot, by rotation of a tool applied onto the tool receptacle, the lever associated with the shaft. If each individual shaft is actuatable, the user must take care that the corresponding pivoting motions of the associated levers result in a vertical displacement of the holding element such that a horizontal position is attained in the working position. The term "horizontal position" is also intended to encompass the case in which the supporting surface of the holding element extends parallel to an X/Y plane of the microdissection device being used. In order to ensure from the outset that such a horizontal position is maintained, it is particularly advantageous to couple the shafts or levers, in terms of their rotation or pivoting motion respectively, by way of the aforesaid coupling elements. In this case a rotation of a shaft or the pivoting motion of a lever results in synchronous rotation of the other shafts, or in synchronous pivoting motion of the other levers, so that the holding element is displaced in terms of its height while maintaining its spatial position.

While each lever is mounted, in a first region, in the frame of the holder, it is advantageous to mount said lever (in another, second region) rotatably in the holding element. For this purpose, usefully, a further shaft is guided by a lever, said shaft being rotatably mounted in the holding element. As a result, the lever and holding element are joined fixedly but pivotably with respect to one another. This embodiment is useful regardless of the nature of the displacement motion of the levers (for example, linear shift or pivoting motion).

Alternatively thereto, embodiments are conceivable in which the holding element abuts against the at least two levers without being fixedly joined to them.

In order to adjust a displacement resistance to vertical displacement of the holding element, it is useful to provide an elastic element, such as a tension spring, tensioned between the frame and holding element.

In the context of the aforesaid configuration in which a lever is fixedly coupled to a shaft rotatably mounted in the frame of the holder, it is useful to configure this coupling releasably in order to allow fine adjustment of the relative position of the lever and shaft. If, for example, two levers each having a shaft are to be present, it may be sufficient to make only one coupling between the lever and shaft releasable, while the other coupling is fixed. The aforesaid fine adjustment serves for precise synchronization of the pivoting motions of the two levers, so that a subsequent vertical displacement of the holding element can be accomplished while exactly maintaining the aforesaid horizontal position.

It is useful to produce the aforesaid coupling between the lever and shaft by clamping; for example, a lever wraps around the shaft in at least one region, so that the lever is clamped onto the shaft. In this case the releasable and securable coupling between lever and shaft can be implemented by additionally providing a releasable set screw. The set screw present in the clamping region then serves to secure and release the clamping or coupling.

For purposes of the aforementioned fine adjustment of the spatial position of the holding element, it is advantageous in particular to configure one of the shafts as an eccentric shaft. Once the coupling between the lever and eccentric shaft is released, the bearing position of the associated lever can then be changed by means of a rotation of the eccentric shaft. No changes need to be made at the other lever/shaft pair. This fine adjustment by rotation of the eccentric shaft, with the coupling between lever and eccentric shaft released, can be accomplished in particular at the factory in the context of manufacture, so that the holder is already exactly aligned for the customer.

The invention further relates to a microdissection device having a holder according to the present invention. Microdissection devices were recited, and explained by way of example, in the introduction to the description. The holder according to the present invention can be used in microdissection devices to ensure at all times that the capture device arranged in the holding element of the holder can always be brought optimally close to the sample carrier of the microdissection device having the sample to be cut out. If the sample carrier defines a (horizontal) X-Y plane, the holder according to the present invention then enables an upward and downward motion of the capture device arranged in the holding element while exactly maintaining the horizontal position, i.e. the plane of the capture device always extends parallel to the aforesaid X-Y plane.

Lastly, the invention relates to a microscope system having a microdissection device according to the present invention. Such microscope systems have likewise already been explained by way of example in the introduction to the description. The microscope system according to the present invention having the microdissection device ensures that samples cut out by means of a laser beam of the microscope system reliably fall into an associated capture element of the capture device. The risk that the associated capture element will not be reached as a result of air movements, or that foreign particles will get into the capture element, is thus minimized.

Further objects, features and advantages of the present invention will become apparent from the detailed description of preferred embodiments that follows, when considered together with the accompanying figures of drawing.

BRIEF DESCRIPTION OF THE DRAWINGS

The invention and its advantages will be further explained below with reference to exemplifying embodiments schematically depicted in the Figures, in which.

DETAILED DESCRIPTION OF THE PREFERRED EMBODIMENTS

The Figures show an embodiment of holder 40 for at least one capture device 30 for collecting a microdissected specimen (see also FIG. 10), capture device 30 to be arranged in a holding element 2, and holding element 2 to be displaceable vertically by way of a stationary frame 1 so that capture device 30 can be brought in optimal proximity to the prepared specimen to be cut, so that the microscopically small cut-out prepared specimens (microdissected specimens) can be reliably collected. The circumstances of microdissection will be discussed in further detail in connection with FIGS. 10 and 11.

Figure 1:
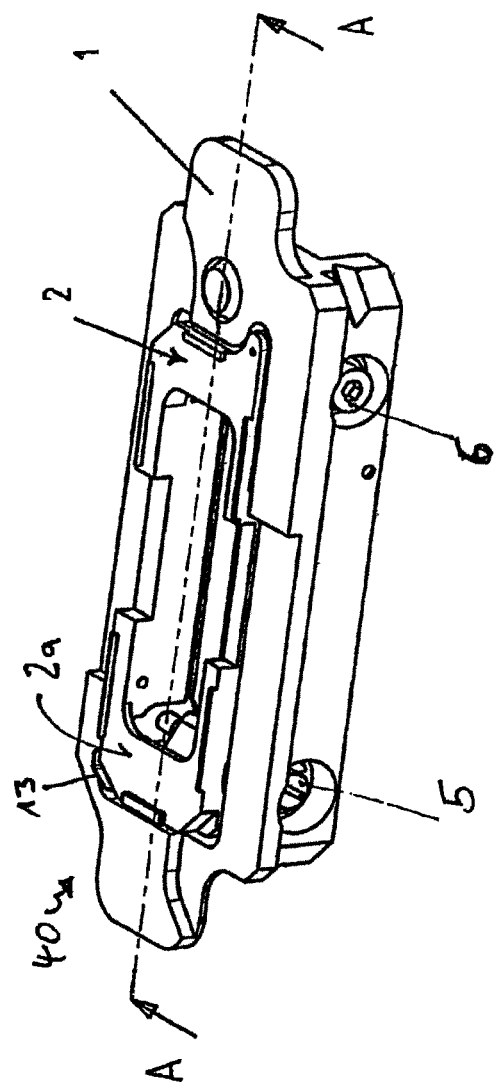
FIG. 1 is a perspective view from above of a holder according to the present invention.

FIG. 1 is a perspective view from above of a holder having a frame 1, a holding element 2 mounted vertically displaceably in the stationary frame 1 (this holding element 2 can also be referred to as a "carrier"), and the two shafts 5 and 6; first shaft 6 is also to be referred to as a primary shaft or leading shaft, and second shaft 5 as an entrained shaft or eccentric shaft. The capture device here is a plate in the form of a standard specimen slide on which, for example, small cup-shaped receptacles (blind holes) are arranged as capture elements 31 (see FIG. 10).

The plate having the capture elements is placed onto supporting surface 2a of holding element 2, and held centeredly at the rim by lateral flanges on holding element 2. Visible in FIG. 1 at the upper left edge of holding element 2 is a sheet-metal spring 13 against which the corresponding corner of the plate is pressed upon insertion thereof into holding element 2. Sheet-metal spring 13 thus presses the plate against the rim flanges on holding element 2, so that the entire plate is secured on holding element 2.

Figure 2:
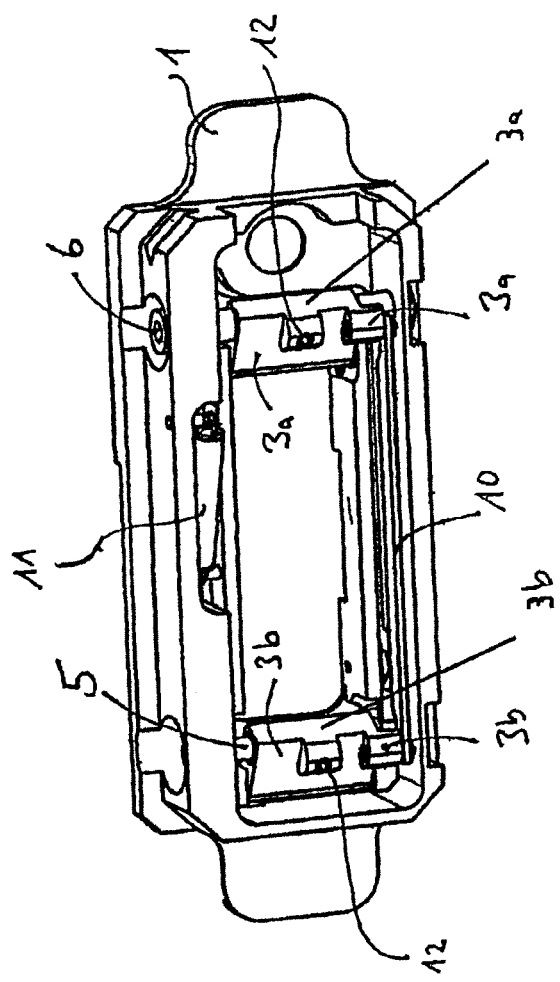
FIG. 2 is a perspective view from below of the holder of FIG. 1.
Figure 3:
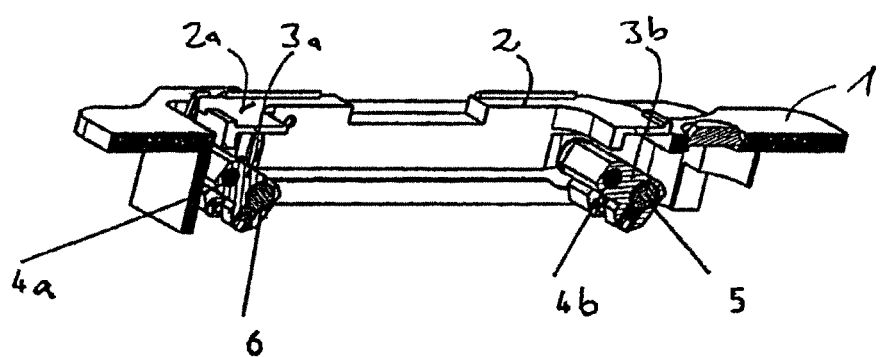
FIG. 3 is a perspective side view of the section along line A-A of FIG. 1.

The physical construction of the holder is clearly evident from the combination of FIGS. 1 to 3. Attached on each of shafts 5 and 6 is a lever 3a and 3b, respectively, which can be, for example, clamped onto the respective shaft 5, 6. Each lever 3a, 3b has, on a side remote from shafts 5, 6, a shaft 4a, 4b (see FIG. 3) that is in turn rotatably joined to holding element 2. The two levers 3a and 3b are furthermore joined to one another by way of a coupling element, in this case a coupling rod 10, in such a way that a pivoting motion of a lever 3a is transferred to the other lever 3b (and vice versa). Coupling rod 10 is in turn joined, by way of shafts not depicted in further detail, to the two levers 3a and 3b in the vicinity of first and second shafts 6 and 5 (see FIG. 2).

As is evident from FIGS. 1 and 2, frame 1 comprises lateral cutouts that enable access to the two shafts 5, 6. This will be discussed in more detail in connection with FIGS. 5 and 6. With regard to the manner of operation of the holder depicted here, it is important firstly that the first (primary) shaft 6 comprise a tool receptacle, for example a hex socket 9. A rotation of the tool (Allen key) results in the manner of operation, discussed below, of holder 40 that is depicted:

A rotation of primary shaft 6 results in a corresponding pivoting motion of lever 3a clamped onto primary shaft 6. Proceeding from a (lower) rest position, primary shaft 6 can be rotated clockwise by means of the tool (Allen key). Lever 3a then pivots, likewise in a clockwise direction, into an (upper) working position (see also FIGS. 8 and 9). Coupling rod 10, attached close to the axis of lever 3a, transfers this pivoting motion of lever 3a to lever 3b, which in turn is clamped onto second entrained shaft 5. The two levers 3a and 3b thus execute codirectional pivoting motions. Because levers 3a, 3b are in turn joined by way of shafts 4a, 4b to holding element 2, a pivoting motion of levers 3a, 3b is converted into a corresponding upward and downward motion of holding element 2.

The clamping of lever 3a, 3b onto shaft 6, 5 associated therewith is advantageously secured using a respective set screw 12. By releasing set screw 12 on lever 3b and rotating eccentric shaft 5, levers 3a and 3b can be adjusted with respect to one another in such a way that an exact horizontal alignment of supporting surface 2a of holding element 2 can be established, in other words, so that supporting surface 2a extends exactly parallel to an X-Y surface (see FIG. 10). This fine adjustment can be performed already during manufacture, but also by the user him- or herself.

To establish a baseline resistance to upward motion of holding element 2, a tension spring 11 is advantageously tensioned between frame 1 and the carrier or holding element 2 (see FIG. 2).

FIG. 3 is a sectioned view along line A-A of FIG. 1. Clearly visible in this sectioned view are shafts 4a, 4b that rotatably join levers 3a and 3b, respectively, to the carrier or holding element 2 (see also FIGS. 8 and 9 in this context).

Figure 4:
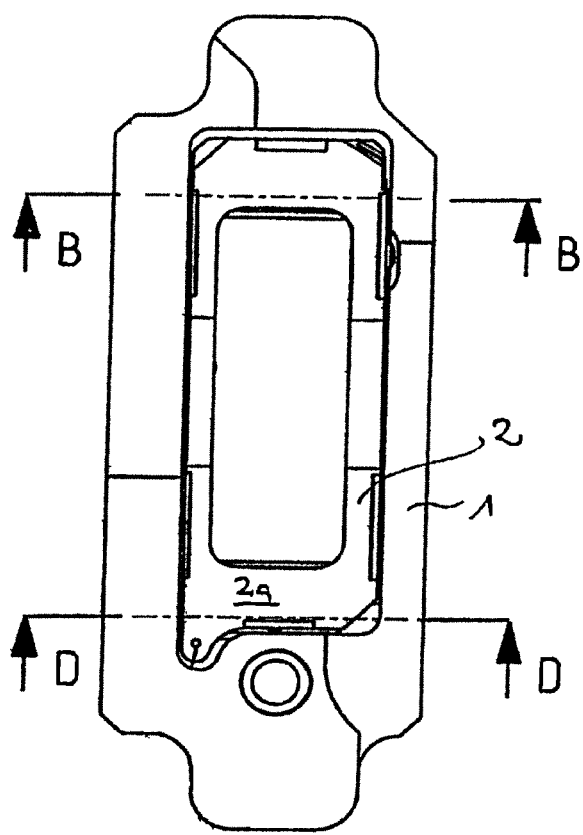
FIG. 4 is a view from above of the holder according to FIG. 1.

FIG. 4 is a view from above of the holder according to FIG. 1. Identical reference characters designate identical elements.

Section line D-D extends through shaft 6, while section line B-B extends through the second, entrained eccentric shaft 5. The corresponding sectioned views are depicted in FIGS. 6 and 5, respectively.

Figure 5:
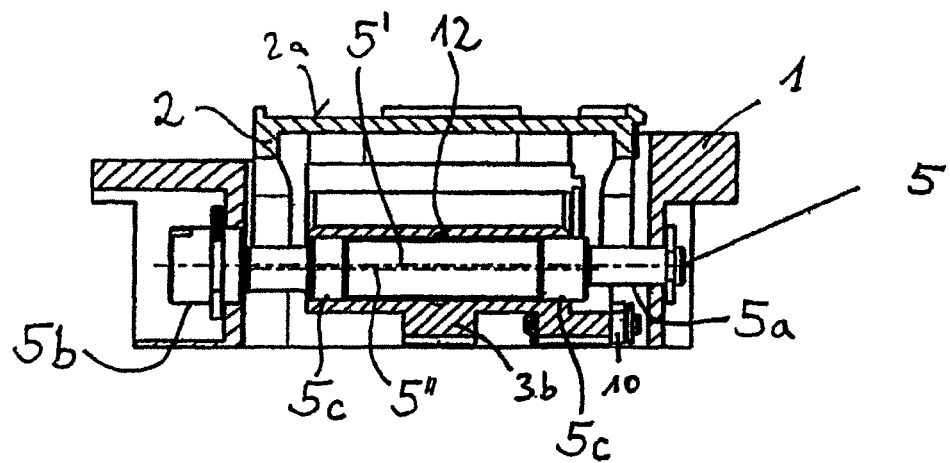
FIG. 5 is a sectioned view along line B-B of FIG. 4.

FIG. 5 is a sectioned view along line B-B, and thus shows a section through eccentric shaft 5. Clamped onto eccentric shaft 5 is entrained lever 3b, which is joined (rotatably about an axis) at one end, in the vicinity of shaft 5, to coupling rod 10. In this Figure as well, identical reference characters designate the same elements as in the previous Figures, so that these elements require no further separate discussion. Further explanations of FIG. 5 may be found below in connection with FIG. 7.

Figure 6:
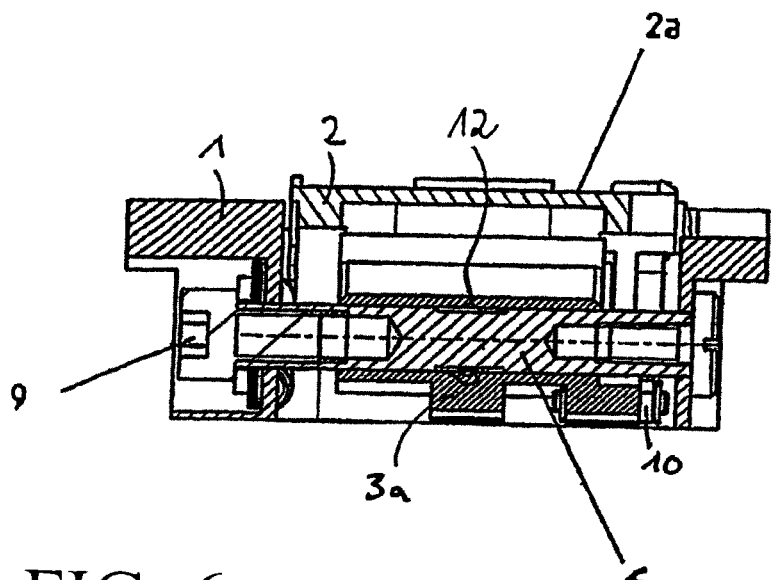
FIG. 6 is a sectioned view along line D-D of FIG. 4.

FIG. 6 is a sectioned view along line D-D of FIG. 4, and thus shows a section through primary shaft 6. A receptacle 9 for a tool (for example, a hex socket) is embodied at one end of shaft 6. Reference may be made to the explanations above for this purpose. Lever 3a is clamped onto shaft 6; set screw 12 for securing the clamped connection is also evident in the view shown in FIG. 6. Located in the vicinity of shaft 6 on lever 3a, on the same side as lever 3b of FIG. 5, is a receptacle for coupling rod 10, which is likewise joined rotatably to lever 3a by way of a shaft. Once again, elements identical to those in the previous Figures are designated with identical reference characters, so that no further discussion in that regard is necessary.

Figure 7:
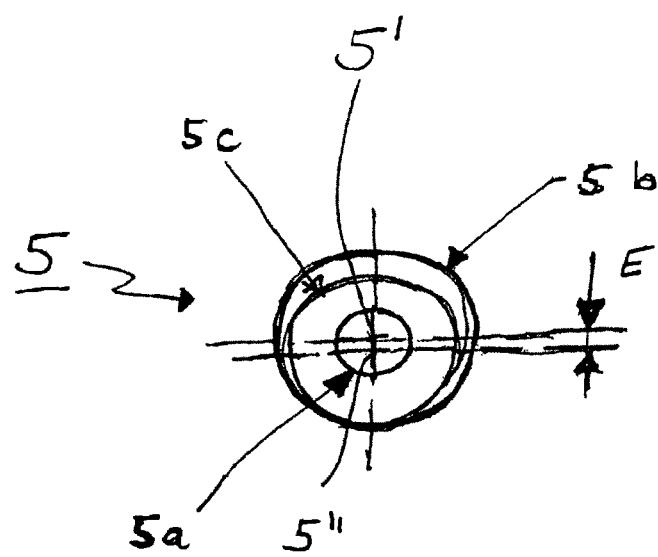
FIG. 7 is a cross-sectional view of shaft 5 of FIG. 5.

FIG. 7 is a schematic cross section through eccentric shaft 5 of FIGS. 5; 5a and 5b designate the periphery of the eccentric shaft at the right and left end, respectively, of eccentric shaft as depicted in FIG. 5. Located at the left end of eccentric shaft 5 is a slot for receiving a screwdriver (see FIG. 5). Located at the center of peripheries 5a and 5b is rotation axis 5' which, upon displacement of the holder by way of a tool actuation of primary shaft 6 (see discussion of FIG. 6), is synchronously co-rotated. Located in the central region of shaft 5 is the eccentric cam, whose periphery is labeled 5c. The axis of the eccentric cam is labeled 5"; it is shifted with respect to rotation axis 5' by an amount equal to eccentricity E. The two axes 5' and 5" are also visible in FIG. 5. Eccentric shaft 5 serves the purpose of fine adjustment of holder 40, advantageously already during assembly or production. Undoing set screw 12 on lever 3b allows eccentric shaft 5 to be rotated so that the bearing position of lever 3b changes. The location of supporting surface 2a can thereby be aligned so that, for example, it extends exactly horizontally between the levers (3a and 3b).

Figure 8:
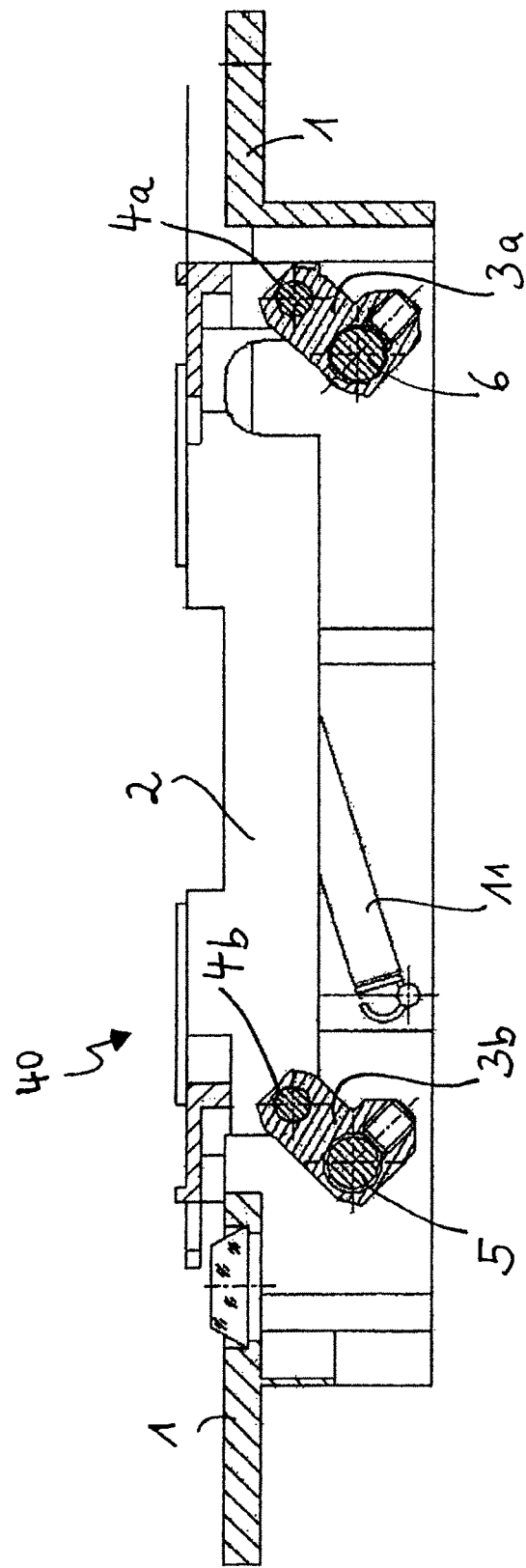
FIG. 8 is a longitudinal section through the holder, with the holding element in the highest position.
Figure 9:
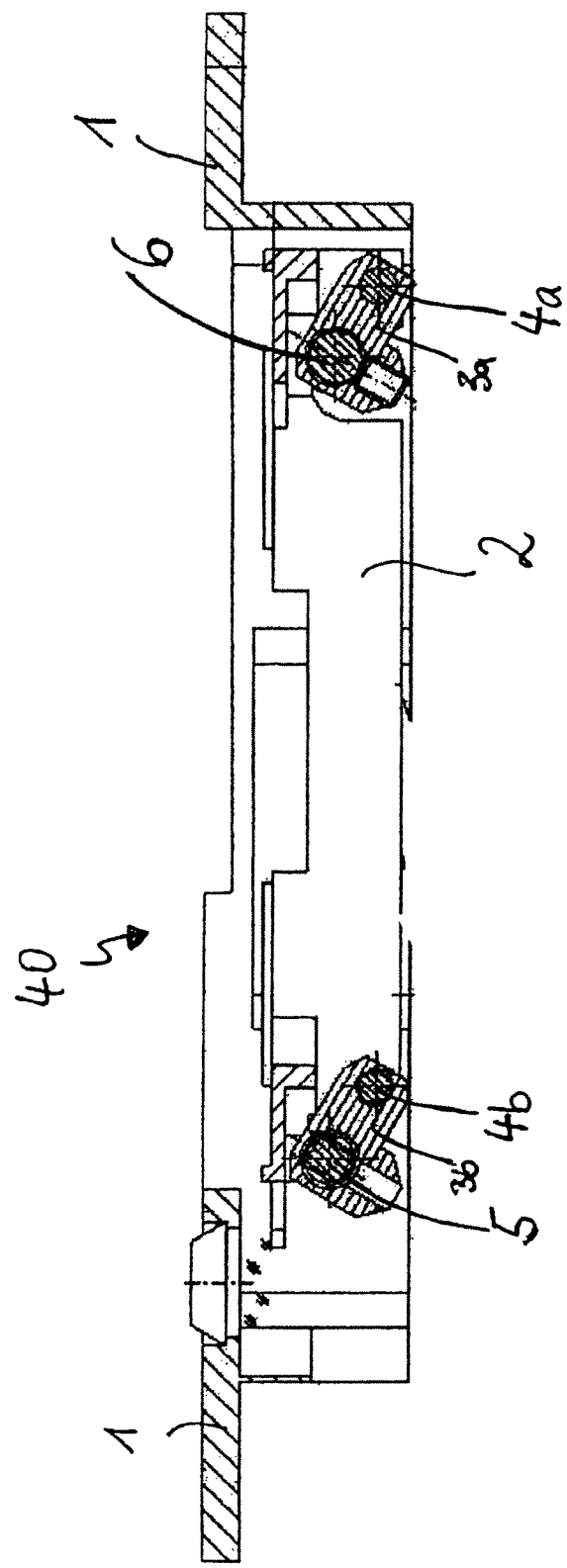
FIG. 9 is a longitudinal section through the holder, with the holding element in the lowest position.

FIGS. 8 and 9, which respectively show the highest and lowest position of the holding element (carrier) 2 in holder 40, will be discussed together. The longitudinal sections through holder 40 schematically show eccentric shaft 5 with its associated lever 3b, as well as primary shaft 6 with its associated lever 3a. As already stated, lever 3b is rotatably joined to the holding element or carrier 2 by way of a shaft 4b, while lever 3a is joined to holding element 2 by way of shaft 4a. With holding element 2 in the highest position (depicted in FIG. 8), tension spring 11 is tensioned. It presents a displacement resistance to displacement. Depending on the desired spacing between the sample to be cut out and capture device 30 carried by holding element 2, the position of holding element 2 can be modified in a vertical direction, while retaining the horizontal orientation, by displacing levers 3a and 3b. In the exemplifying embodiment being dealt with here, this is accomplished by pivoting of the levers. As already explained at various points, the displacement can be achieved in a technically different fashion, for example by the fact that the levers execute a synchronous linear shift as a result of which holding element 2 is displaced vertically. FIG. 9 shows levers 3b and 3a pivoted about shafts 5 and 6, respectively; holding element 2 now assumes its lowest position. FIGS. 8 and 9 serve solely to illustrate the upward and downward motion of holding element 2 relative to the stationary frame 1, so that further details, for example coupling element 10, are not depicted here.

Figure 10:
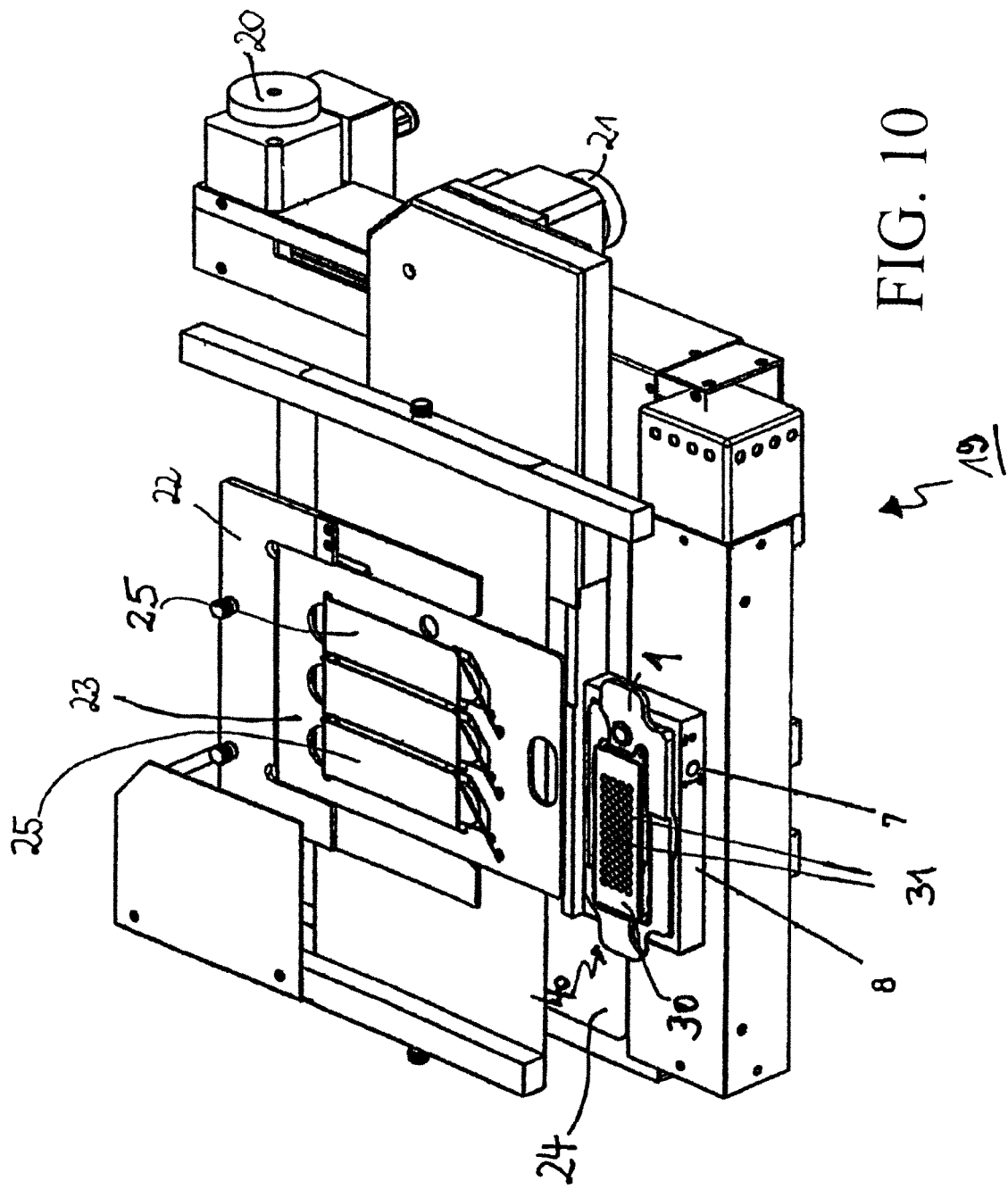
FIG. 10 shows a microdissection device having an X/Y stage having a receptacle for specimen slides and a holder having a capture device for collecting a microdissected specimen.

FIG. 10 shows a microdissection device, depiction of a microscope having been omitted. A double X-Y stage is depicted, having an upper part 22 (holding plate) and a lower part 24, the X and Y drive units of the X-Y stage not being explicitly labeled here. The X and Y drive units of holder 40 are labeled 20 and 21, respectively. The upper and lower part 22 and 24, respectively, of X-Y stage are fixedly joined by way of a spacer. Holder 40 moves in the cavity formed in this fashion. A holding plate 22 for a receptacle 23 for specimen slides 25 is located on the X-Y stage. A variety of specimen slides 25 are used for microdissection. For example, a film can be stretched over a metal frame or onto a slide. The prepared specimens to be cut out by microdissection are located on the film. The film can in turn be cut, for example, by means of a focused laser beam. Once a selected X-Y position has been arrived at with stage 24, a specific specimen slide 25 is located below the microscope objective (not depicted), so that the region of interest can be imaged and viewed in magnified fashion, or evaluated using image processing technology. The prepared specimen to be cut out is suitably marked, i.e., for example, an individual or preshaped cut line is placed around the prepared specimen to be cut out. A focused laser beam is then guided along the cut line. The microdissected specimen, i.e. the prepared specimen present on the cut-out film, falls downward by gravitation into a capture element. For this purpose, holder 40 depicted in FIG. 10 is moved beneath the relevant specimen slide 25, and under the cutting region thereon, by means of X-Y drive units 20 and 21, in such a way that the microdissected specimen can fall into one of the depicted capture elements 31 of capture device 30.

To ensure that the microdissected specimen, having an extension of only a few micrometers and of correspondingly light weight, is not moved by air movements into a region outside a capture element 31, and that other particles present in the air cannot get into the intended capture element 31, it is necessary to place the relevant capture element 31, and thus the entire capture device 30, in the closest possible proximity beneath specimen slide 25. The invention makes it possible to adjust this spacing optimally, depending on the arrangement of specimen slide 25 and holding plate 22 and depending on the use of the (various) capture devices 30. For this purpose, it is necessary to ensure that holding plate 22 and specimen slide 25 extend, over the entire X-Y region, exactly parallel to the surface of capture device 30 and to supporting surface 2a of holding element 2. The capture device can then, by means of the vertical displaceability of holding element 2, be moved as close as possible below specimen slide 25. For this purpose, as described above in detail, shaft 6 is rotated by means of a tool (Allen key) that is inserted through opening 7 of receiving frame 8 into tool receptacle, resulting in an up/down movement of holding element 2 and thus of capture device 30.

Figure 11:
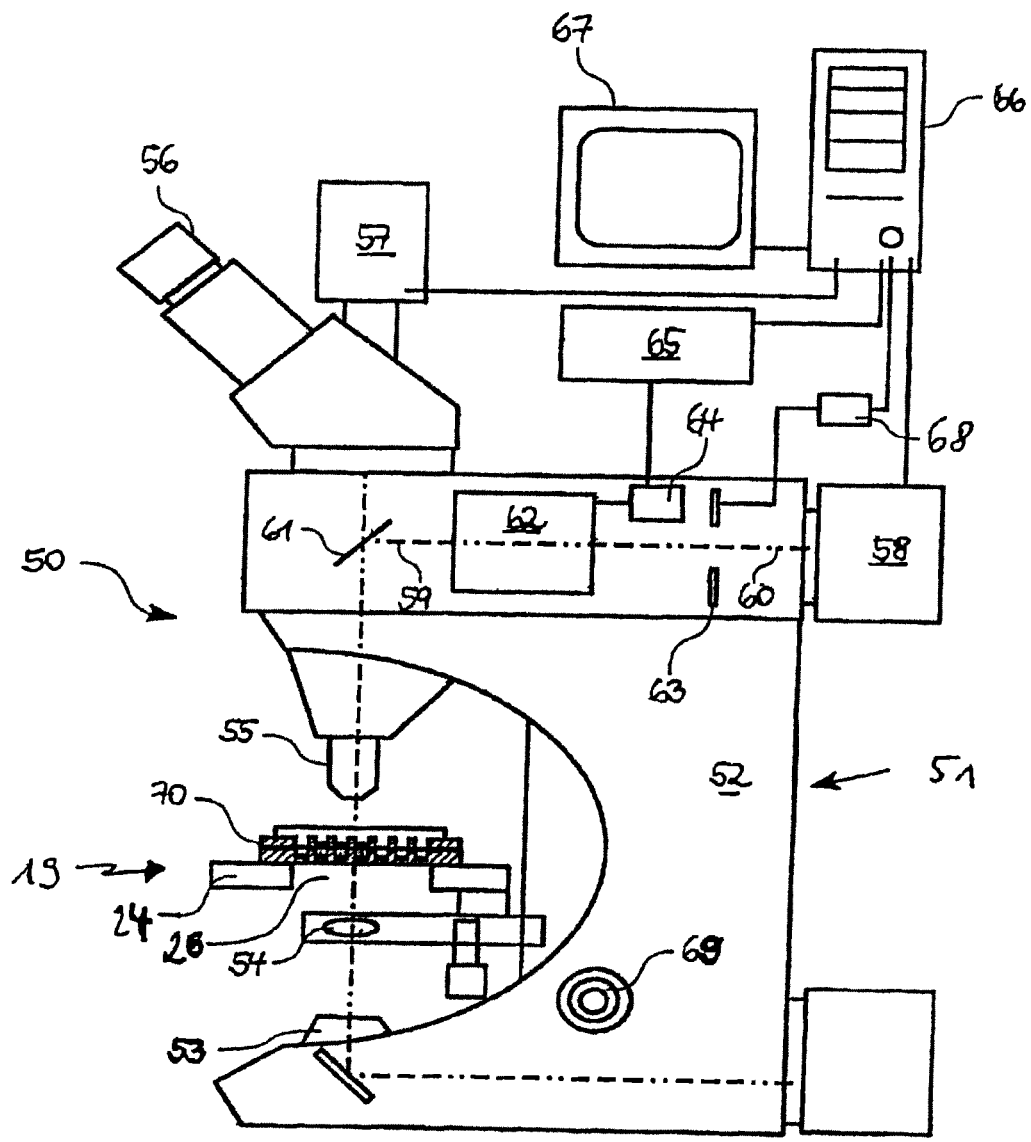
FIG. 11 shows a microscope having a microdissection device.

FIG. 11 shows, very schematically, a microscope system having a microscope dissection device using an upright microscope. Further details about such a microscope system may be gathered from WO 2008/034833 A2, already recited in the introduction to the description, to which reference is expressly made here with regard to the construction and manner of operation of the microscope system.

FIG. 11 shows a microscope system 50 for microdissection, having a microscope 51 and a microdissection device 19.

With the system depicted, a laser beam can be guided over a biological sample, located in stationary fashion on an X/Y stage 24, in order to cut out a prepared specimen. The stand of microscope 51 is labeled 52. X/Y stage 24 can be shifted in motorized fashion in the X-Y plane. It serves here to carry a device 70 for receiving biological material. This device 70 will be discussed separately later.

In the present exemplifying embodiment, the biological material is illuminated from below by transmitted light. X/Y stage 24 has for this purpose a frame-shaped configuration with an opening 26. Microscope 51 is consequently a transmitted-light microscope having an illumination system 53 and a condenser 54 that are arranged below stage 24. The illumination unit is depicted only very schematically. In known fashion, the object (sample) illuminated in this fashion is imaged at high magnification for an observer by means of a main objective (not separately labeled), tube, and eyepiece 56. Alternatively or additionally, a camera 57 can be provided.

A laser beam 59 generated by a laser 58 (here a UV laser) is coupled into a reflected light illumination beam path having an optical axis 60, and proceeds through a laser scanner 62. From there it travels by way of a deflection element 61 to main objective 55 of microscope 51, through which laser beam 59 is focused onto the biological sample in device 70 for receiving biological material. With the aid of laser scanner 62, the laser beam can be moved over the sample while the other microscope components, as well as X/Y stage 24, remain unchanged in terms of their position. Deflection element 61 is preferably a dichroic mirror or beam splitter that allows the observation beam path emerging from the sample to pass through to camera 57 or eyepiece 56. In addition to deflection element 61, further optical components can be arranged as necessary in the propagation direction of laser beam 59. The number 63 designates an adjustable diaphragm by means of which the aperture of laser beam 59 is adjustable.

The movement of the focused laser beam over the sample that is to be cut out, in order to generate a cut line, is accomplished by means of laser scanner 62. Laser scanner 62 is connected for this purpose to a motor 64 that in turn is connected to a control unit 65 that is controlled by a control computer 66. At the same time, computer 66 receives signals from control unit 65. A monitor 67 is connected to the computer, as well as the aforementioned camera 57, so that images of the sample sensed by the camera can be displayed on monitor 67. With this system it is possible to observe the sample that is to be cut out, and to observe and control the cutting operation. For example, control computer 66 can issue a trigger signal to laser 58 in order to begin the cutting operation. The output power and further characteristics of the laser beam can furthermore be controlled with the aid of computer 66. Aperture control motor 68 can additionally be controlled by computer 66. Lastly, the computer can apply control to an autofocus unit (not depicted) for laser beam 59. Computer 66 is connected for this purpose to the aforesaid elements (58, 68, 65).

In order to define a cut line, it is possible to provide an external operating element (not depicted) such as a computer mouse, with the aid of which a (predefined or individual) cut line can be placed or drawn on monitor 67 around the sample to be cut out. Automatic generation of cut lines using image-processing methods is also possible. In accordance with the defined cut line, laser beam 59 is correspondingly moved over the sample by means of control unit 65, motor 64, and laser scanner 62, so that the focused laser beam cuts out the selected sample piece. During the cutting operation, X/Y stage 24 is not moved in a horizontal direction. Alternatively, the cut line could be generated by moving X/Y stage 24 while the laser beam is stationary.

By means of focus adjuster 69 on stand 52 of microscope 51, focusing of the laser beam can be utilized as an alternative to use of an autofocus unit, or in addition to coarse focusing.

After completion of the cutting operation, the sample located on the cut-out piece of film is completely separated from its surroundings and can thus fall, in response to the force of gravity, into a capture element 31 inside device 70.

In the present Application—in contrast to the document WO 2008/034833 A2 cited in this connection—device 70 is a combination of a holder 40, for at least one capture device for collecting a microdissected specimen, with a receptacle 23 for specimen slides 25 for receiving samples that are to be cut out. Alternatively, microdissection device 19 depicted in FIG. 10 can also be incorporated into microscope system 50 of FIG. 8, replacing components 24, 26, and 70. It is essential that holder 40 permit vertical adjustment of the received capture device with its capture elements, so that the relevant capture element can be brought as close as possible to the sample that is to be cut out. Device 70 for receiving biological material may be imagined for this purpose as, for example, a combination of holder 40 (already discussed in detail) with a capture device 30 corresponding in shape and size to a specimen slide, and with a specimen slide 25, arranged congruently thereabove, that contains biological material present on a film.

The foregoing description of preferred embodiments of the invention has been presented for purposes of illustration and description only. It is not intended to be exhaustive or to limit the invention to the precise form disclosed, and modifications and variations are possible and/or would be apparent in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by reference to the claims appended hereto and that the claims encompass all embodiments of the invention, including the disclosed embodiments and their equivalents.

PARTS LIST

1 Frame
2 Holding element, carrier
2a Support surface
3a, 3b Lever
4a, 4b Shaft
5 Second shaft, eccentric shaft
5' Rotation axis
5" Axis of eccentric cam
5a Periphery
5b Periphery
5c Periphery of eccentric cam
6 First shaft, primary shaft
7 Opening
8 Receiving frame
9 Tool receptacle, hex socket
10 Coupling element, coupling rod
11 Tension spring
12 Set screw
13 Sheet-metal spring
19 Microdissection device
20 X drive unit 21 Y drive unit
22 Holding plate, upper part of X-Y stage
23 Receptacle for specimen slide
24 Lower part of X-Y stage
25 Specimen slide
26 Stage opening
30 Capture device
31 Capture elements
40 Holder
50 Microscope system
51 Microscope
52 Microscope stand
53 Illumination system
54 Condenser
55 Main objective
56 Eyepiece
57 Camera
58 Laser
59 Laser beam
60 Optical axis
61 Deflection element
62 Laser scanner
63 Diaphragm
64 Motor
65 Control unit
66 Control computer
67 Monitor
68 Diaphragm control motor
69 Focus adjuster
70 Device for receiving biological material
E Eccentricity

What is claimed is:

1. A holder for at least one capture device for collecting microdissected specimens cut out from a microscopic sample, the holder being configured to be inserted into a laser microdissection device, the holder comprising:
 a frame having at least one lateral cutout,
 a holding element mounted in the frame, the holding element being vertically displaceable relative to said frame and configured to receive at least one capture device for collecting at least one microdissected specimen,
 a first shaft rotatably mounted in a lateral cutout of the frame,
 a second shaft rotatably mounted in the frame,
 a first lever coupled to the first shaft and configured to execute a pivoting motion,
 a second lever coupled to the second shaft and configured to execute a pivoting motion,
 one or more coupling elements that couple the first lever and the second lever,
 a third shaft coupled to the first lever and the holding element, and
 a fourth shaft coupled to the second lever and the holding element,
 wherein for vertical displacement of the holding element,
  a rotation of the first shaft pivots the first lever and a pivoting motion of the first lever is transferred to the second lever by the one or more coupling elements to execute a codirectional pivoting motion of the second lever, and
  the pivoting motion of the first lever is transferred to the third shaft and the pivoting motion of the second lever is transferred to the fourth shaft, thereby actuating a vertical displacement of the holding element coupled to the third shaft and the fourth shaft.

2. A holder for at least one capture device for collecting microdissected specimens cut out from a microscopic sample, the holder comprising:
 a holding element in which the at least one capture device is to he arranged, the holding element being transferable into a working position in order to collect at least one microdissected specimen,
 wherein the holding element is mounted by way of at least two levers in a frame of the holder, and is vertically displaceable relative to said frame by way of a displacement of the levers. and
 wherein each lever is coupled to a respective shaft that is rotatably mounted in the frame of the holder,
 wherein the levers are coupled in their displacement motion by way of one or more coupling elements,
 wherein the levers execute a pivoting motion in their displacement, and
 wherein for vertical displacement of the holding element, at least one of the shafts comprises a tool receptacle in order to pivot, by rotation of a tool applied onto the tool receptacle, the lever associated with the at least one of the shafts.

3. The holder according to claim 2, wherein the shafts are coupled in their rotation by way of one or more coupling elements.

4. The holder according to claim 2, wherein each lever is coupled to an additional shaft that is rotatably mounted in the holding element.

5. The holder according to claim 2, wherein a displacement resistance for the vertical displacement is defined by an elastic element tensioned between the frame and holding element.

6. The holder according to claim 2, wherein for fine adjustment of a relative position of a lever and a shaft, a coupling between the lever and the shaft is releasable.

7. The holder according to claim 2, wherein a coupling between a lever and a shaft is produced by clamping an additional lever onto the shaft.

8. The holder according to claim 6, wherein a releasable set screw is provided to secure the relative position between the lever and the shaft.

9. The holder according to claim 2, wherein one of the shafts is configured as an eccentric shaft.

10. The holder according to claim 9, wherein once a coupling between the lever and the eccentric shaft is released, a bearing position of the lever can be changed, by a rotation of the eccentric shaft, for fine adjustment of a spatial position of the holding element.

11. A microdissection device having a holder according to claim 2.

12. A microscope system having a microdissection device according to claim 11.

13. The holder according to claim 2, wherein the tool receptacle is accessible from an outside of the holder.

14. The holder according to claim 1, wherein the first shaft has a tool receptacle accessible from an outside of the holder, the tool receptacle configured to receive a tool for actuating the rotation of the first shaft.

* * * * *